United States Patent [19]

Stout

[11] Patent Number: 4,671,267
[45] Date of Patent: Jun. 9, 1987

[54] GEL-BASED THERAPY MEMBER AND METHOD

[75] Inventor: Edward I. Stout, 5207 W. 76th St., Prairie Village, Kans. 66208

[73] Assignee: Edward I. Stout, Prairie Village, Kans.

[21] Appl. No.: 891,632

[22] Filed: Aug. 1, 1986

Related U.S. Application Data

[63] Continuation of Ser. No. 615,881, May 30, 1984.

[51] Int. Cl.⁴ .............................................. A61L 15/01
[52] U.S. Cl. ................................... 128/156; 128/155; 128/380; 128/381; 128/382; 128/402; 604/291; 604/304; 604/307; 604/308
[58] Field of Search ............... 128/155, 156, 380, 381, 128/382, 402; 604/291, 304, 307, 308; 424/DIG. 13

[56] References Cited

U.S. PATENT DOCUMENTS

| | | | |
|---|---|---|---|
| 1,044,817 | 11/1912 | Pond . | |
| 3,308,491 | 3/1967 | Spence . | |
| 3,548,420 | 12/1970 | Spence . | |
| 3,663,973 | 5/1972 | Spence | 3/20 |
| 3,780,537 | 12/1973 | Spencer | 62/530 |
| 3,849,238 | 11/1974 | Gould et al. | 128/156 |
| 3,858,379 | 1/1975 | Graves et al. | 3/20 |
| 3,943,045 | 3/1976 | Cordrey et al. | 204/159.22 |
| 3,963,685 | 6/1976 | Abrahams | 526/230 |
| 3,997,660 | 12/1976 | Kopecek et al. | 424/78 |
| 4,045,387 | 8/1977 | Fanta et al. | 128/156 |
| 4,055,188 | 10/1977 | Pelton | 128/402 |
| 4,074,039 | 2/1978 | Lim et al. | 128/156 |
| 4,076,921 | 2/1978 | Stol et al. | 128/156 X |
| 4,092,982 | 6/1978 | Salem | 128/82.1 |
| 4,243,041 | 1/1981 | Paul | 128/402 |
| 4,377,160 | 3/1983 | Romaine | 128/156 |
| 4,393,048 | 7/1983 | Mason, Jr. et al. | 424/DIG. 13 |

FOREIGN PATENT DOCUMENTS

2099704 12/1982 United Kingdom ................ 128/156

Primary Examiner—William R. Dixon, Jr.
Assistant Examiner—Steven Capella
Attorney, Agent, or Firm—Schmidt, Johnson, Hovey & Williams

[57] ABSTRACT

Improved therapy members useful for treating of sprains, muscle aches, orthopedic and skin injuries such as burns and other wounds are provided which make use of a pliable, self-sustaining, moisture sorbing gel including a humectant such as glycerin entrapped within a synthetic resin polymer matrix (e.g., a matrix containing acrylic acid or acrylamide monomer moieties). In one preferred embodiment, a body of the gel is encased within heat and moisture-permeable stretch fabric, and securing ties or the like are provided to permit the composite to be conformed to a body part and held in place. In use, such therapy wraps are either heated (as in a microwave oven) or refrigerated, so as to provide appropriate thermal treatment; it has been found that the preferred gel of the invention retains its pliability and other physical properties over a very broad temperature range, such as −20° to 305° F., and therefore the wraps of the invention can be used in many treatment contexts. It has also been discovered that the gel material can be applied directly to injured skin to in effect create a temporary skin with ideal air permeability. Furthermore, the moisture absorbing and desorbing properties of the gel create a moisture equilibrium between the gel, damaged skin and the atmosphere, thus promoting rapid healing.

17 Claims, 4 Drawing Figures

GEL-BASED THERAPY MEMBER AND METHOD

This application is a continuation of application Ser. No. 615,881, filed May 30, 1984.

BACKGROUND OF THE INVENTION

1. Field of the Invention

The present invention is broadly concerned with gel-based therapy members and methods of use thereof wherein the gel has outstanding pliability and moisture sorbing properties over a very broad temperature range. More particularly, it is concerned with such therapy members and methods which make use of a gel having a water soluble humectant entrapped within a polymeric matrix, the latter preferably including acrylic acid or acrylamide monomer moieties.

2. Description of the Prior Art

The treatment of many injuries such as sprains, contusions or dislocations where immediate swelling is common typically involves application of cold ice compresses or other materials to slow the flow of blood to the injured site, thus reducing swelling. After the initial trauma and swelling due to the injury have subsided, however, it is often advisable to apply heat to the injured area to promote healing. Here again, a number of expedients have been used in the past for this purpose, including hot towels or heating pads.

It has also been proposed in the past to provide therapeutic wraps or compresses which make use of gel materials. For example, U.S. Pat. No. 4,055,188 describes a therapeutic wrap which includes an elongated, pocketed member having refrigerant gel in the pocket. In use, the gel is refrigerated and placed in the pockets, whereupon the complete device is wrapped about an area to be treated. Similar devices are described in U.S. Pat. Nos. 4,092,982 and 4,243,041.

U.S. Pat. No. 3,780,537 describes a hot and cold compress device which includes an outermost, liquid impervious envelope containing a liquid gel designed to maintain its gel-like consistency over a temperature range of from about 0–212° F.

While the gel-based therapy wraps of the above identified patents have been proposed, they are deficient in a number of respects. For example, it is desirable that a therapy wrap maintain its desirable pliability and other physical properties over as broad a temperature range as possible. This permits stocking of only a single kind of therapy wrap for a given type of injury, which can be used either for heating or cooling therapy. In addition, a desirable gel-based therapy member should be non-flowing, i.e., the gel component should maintain its consistency and self-sustension even if the composite is punctured. In addition, many prior gels are deficient in that they have poor moisture absorption characteristics, or are encased within a material which in effect forms a moisture barrier. Desirably, a gel used in a therapy wrap should be able to absorb and desorb moisture as necessary, in order to maintain a moisture equilibrium at the patient's skin and, in the case of heat therapy, to give a desirable "moist heat" effect.

In addition, a number of gel-based materials have been proposed for use in cushion or pad devices. For example, U.S. Pat. Nos. 3,858,379, 3,308,491, 3,663,973 and 3,548,420 are concerned with various types of pad constructions. Finally, highly successful pad composites commercialized as "Elastogel ™ Seat Cushions" have been distributed by Southwest Technologies, Inc. of Kansas City, Mo. These pads comprise a layer of soft polymeric gel covered with a four-way stretch, breathable, moisture-pervious fabric. The gel employed in these pad devices (which are used, for example, as wheel chair seat pads) comprises a quantity of glycerin entrapped within an acrylamide polymeric matrix.

It has also been known in the past to provide various types of materials as burn dressings. As is well known, severe burns are excruciatingly painful for a patient, and can present severe and even life threatening problems if the burned skin sloughs off exposing subdermal layers. In the context of a burn treatment device, it would be desirable to provide a dressing or covering which would in effect form a substitute "skin" for the patient. This would require that the dressing "breathe", or have adequate air permeability characteristics. At the same time, it is desirable that proper moisture conditions be maintained for prompt healing of burned skin; for example, an appropriate dressing should not absorb excessive moisture and thus dry the burned skin, inasmuch as this will inhibit proper healing.

In short, while therapy members such as therapeutic wraps and dressings have been proposed in the past, and in certain instances gel-based formulations have been used, these prior devices and methods of use thereof have presented a number of significant problems.

SUMMARY OF THE INVENTION

The present invention has as its aim provision of greatly improved therapy devices such as therapy wraps and dressings, as well as corresponding methods of use thereof.

For example, the invention comprehends a method of treating a body part of a patient which comprises the steps of providing a therapy member including a body of self-sustaining pliable gel. The gel broadly includes a water soluble humectant entrapped within a polymeric matrix having therein acrylic acid or acrylamide monomer moieties. Further, the gel is characterized by the properties of maintaining its self-sustension and pliability over a relatively broad temperature range of from about −20° to 350° F., and of absorbing and desorbing moisture.

The next step of the method involves pretreating the therapy member by altering the temperature of the gel body therein to a level significantly below or above body temperature while maintaining the pliability and moisture sorbing characteristics of the gel body. Finally, the pretreated therapy member is applied to the body part in question by placing the gel body in close, generally conforming proximity to the body part for heating or cooling thereof as the case may be.

In preferred forms, a moisture and heat permeable stretchable cloth is interposed between the gel body and the body part, which typically involves encasing the entire gel body in a cloth of these characteristics. For convenience, it is often desirable to affix the pretreated therapy member to the body part for a period of time, and to this end elongated ties or other expedients are employed for securing the gel-based therapy member in place.

The gel material forming a part of the preferred therapy members of the invention advantageously include a humectant selected from the group consisting of glycerin, ethylene glycol, propylene glycol, dimethyl sulfoxide and dimethyl formamide. In addition, the humectant is preferably present at a level of from about 20 to 85% by weight in the gel body, and more preferably from about 50 to 75% by weight. The most preferred polymeric matrix is selected from the group consisting of polymers, copolymers, and terpolymers containing acrylic acid or acrylamide monomer moieties, and most preferably is a polymer of acrylamide.

A wide variety of gel thicknesses can be employed in the context of the invention, but generally speaking the gel should have a thickness of from about ¼ to 1½ inches.

The pretreatment step as noted above involves altering the temperature of the gel body. This can be done by a variety of means. For example, the gel body (and encasing stretch fabric) can be simply placed in a microwave or conventional oven and heated for an appropriate period of time. Alternately, the therapy member can be placed in a freezer in order to significantly lower the temperature of the gel body. In alternate refrigeration procedures, the therapy member may be placed within a plastic bag or other water-impervious container, and the latter is then simply emersed in ice water. Generally speaking, the gel body temperature should be altered to a temperature within the range of from about $-20$ to $350°$ F.

It has also been found that the preferred gel material of the invention provides an excellent dressing for the treatment of burned or otherwise injured skin. In this case a thin (for example from about 0.05 to 0.5 inches) layer of the gel material is hermetically sealed in a sterile package, and in use is simply directly applied to injured skin, without any intermediate cloth covering or the like. This gel body is generally left in contact with the burned skin for a period of from about 2 to 21 days, and in effect forms a "second skin" for the patient. The air permeability characteristics of the gel body approximate those of living human skin, and moreover the moisture sorbing characteristics of the gel creates a desirable equilibrium between the burned skin, gel and atmosphere Furthermore, when the gel absorbs moisture from the skin, a humectant exchange with the skin occurs which tends to keep skin moisture levels relatively low, and this in turn inhibits bacterial growth. Finally, the clear nature of the gel permits continuous monitoring of the injured skin. All of these conditions promote rapid healing.

The absorbance (or water holding capacity) of the gel dressing may be enhanced by incorporating therein products referred to as "super absorbants", such as hydrolyzed starch-acrylonitrile graft copolymers described in U.S. Pat. No. 3,935,099.

Products of this type will often exhibit absorbance of 50 to 1,000 g of distilled water per gram of product.

DESCRIPTION OF THE PREFERRED EMBODIMENTS

Figure 1:
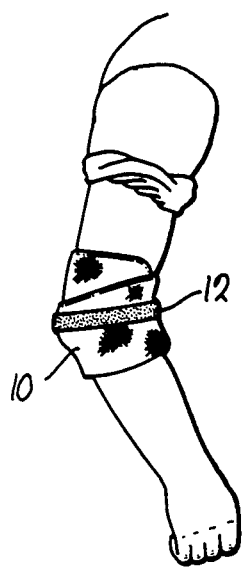
FIG. 1 is a side view illustrating an elongated therapy wrap in accordance with the invention wrapped about an injured patient's elbow.

As noted above, the therapy wraps and skin dressings in accordance with the present invention include a water soluble humectant entrapped within a polymeric matrix. While a wide variety of formulations can be employed to good effect in the context of the invention, it has been found that certain specific components and ranges give the most satisfactory results. For example, in the case of therapy wraps and skin dressings, the polymeric matrix is most preferably formed of acrylamide, whereas the humectant is in the form of glycerin. Other components, such as methylene-bisacrylamide cross-linking agent, ammonium persulfate initiator and citric acid are also employed in such preferred formulations.

The following table sets forth the most preferred formulations, as well as desirable approximate ranges of use for the respective constituents, both in the case of therapy wraps and skin dressings:

TABLE I

| Constituent | [1]Therapy Wrap Preferred | Range | [1]Skin Dressing Preferred | Range |
|---|---|---|---|---|
| Citric acid | 0.02% | 0.01 to 0.10 | 0.02 | 0.01 to 0.10 |
| Ammonium persulfate | 0.04 | 0.01 to 0.2 | 0.04 | 0.01 to 0.2 |
| N,N methylene-bisacrylamide | 0.09 | 0.04 to 0.2 | 0.08 | 0.02 to 0.15 |
| [2]acrylamide | 17.97 | 10.0 to 30.0 | 14.42 | 10.0 to 25.0 |
| [2]water | 17.97 | 10.0 to 80.0 | 14.42 | 10.0 to 50.0 |
| glycerin | 63.91 | 20.0 to 85.0 | 71.00 | 50.0 to 85.0 |
| [3]Super absorbant | — | — | 0.02 | 0.10 to 0.60 |

[1]All data in percentages by weight
[2]Premixed as a 50% by weight solution of acylamide and water
[3]Hydrolyzed starch-acrylonitrile graft copolymer (an optional ingredient)

In fabricating the gel bodies using the above constituents, it is desirable to admix and stir all of the constituent materials at a temperature of above about 65° Fahrenheit, whereupon the liquid mixture is into an appropriate mold and allowed to set for a period of at least about one-half hour to forty-five minutes, and more preferably for about twenty-four hours. At the end of this time, the gel can be cut to an appropriate size and configuration. The gel body can then be encased within an appropriate stretch fabric to form a therapy wrap; in the case of a skin dressing a gauze or other backing can be applied to the gel body, and the entire composite can be packaged in a sterile container or package.

While the above table sets forth the preferred constituents and ranges, those skilled in the art will appreciate that the invention is not so limited. For example, while the preferred cross linking agent is N,N methylene-bisacrylamide (MBA), other types of cross linking agents can be employed such as N-methylolacrylamide, allyl methacrylate, and ethylene glycol dimethacrylate. Moreover, while ammonium persulfate is a suitable initiator for the polymerization reaction, the use of an initator is not essential. Finally, while acrylamide is the preferred matrix-forming material, other similar materials can also be used, such as acrylic acid. In such cases, the acrylic acid should be used at a level of from about 10 to 20% by weight, humectant at a level of from about 20 to 80% by weight, water at a level of from about 20 to 70% by weight, MBA at a level of from about 0.01 to 0.04% by weight, and initiator at a level of from about 0.01 to 0.04% by weight. The most preferred ranges are from about 14 to 18% acrylic acid, from about 50 to 76% humectant, from about 8 to 22% water, and from about 0.01 to 0.3% cross linking agent.

Those skilled in the art will also appreciate that by proper selection of monomer and by varying the ratio of monomer (or monomers) relative to the cross linking agent and humectant, the hardness and toughness of the gel material may be altered and controlled. Accordingly, if relatively high moisture absorption characteristics are desired, the gel should be formulated to have a high percentage of humectant and a relatively low percentage of cross linking agent in order to produce a soft, relatively rubbery gel. If more firmness is required, the amount of humectant may be reduced, whereas the amount of cross linking agent should be increased.

The following Examples set forth a number of specific gel formulations in accordance with the invention, as well as the properties thereof.

EXAMPLE 1

A total of 16 separate gel formulations were prepared using the constituents and amounts set forth in Table II. In each case the acrylamide or acrylic acid was initially mixed with water, followed by addition of the MBA and $K_2S_2O_8$ initiator. The resulting solution was then added to the desired type and quantity of humectant with vigorous mixing. A solution of initiator was then added and the resulting solution was thoroughly mixed and poured into a mold of desired shape. The mixture was kept in the mold for various periods of from one to twenty-four hours. Table II sets forth the specific components of the various formulations, as well as the final properties of the gel products.

TABLE II

| Humectant Type | Wt., g | 50% Acrylamide Wt., g | MBA Wt., g | $K_2S_2O_8$ Wt., g | Properties |
|---|---|---|---|---|---|
| 1. Glycerin | 5448 | 1362 | 5.0 | 3.3 | Soft gel |
| 2. Glycerin | 5448 | 1362 | 3.3 | 3.3 | Very soft gel |
| 3. Glycerin | 5448 | 1362 | 10.0 | 3.3 | Firm rubbery solid |
| 4. Glycerin | 2270 | 454 | 5.0 | 3.3 | Firm rubbery solid |
| 5. DMSO* | 55 | 16 | 0.05 | 0.03 | Very soft gel |
| 6. DMSO | 55 | 20 | 0.10 | 0.06 | Soft gel similar to #1 |
| 7. DMSO | 55 | 22 | 0.50 | 0.06 | Firm rubbery solid |

| Humectant Type | Wt., g | $H_2O$ Wt., g | Acrylic Acid Wt., g | MBA Wt., g | $K_2S_2O_8$ Wt., g | Properties |
|---|---|---|---|---|---|---|
| 8. Glycerin | 55 | 6 | 10 | 0.10 | 0.06 | Soft rubbery gel |
| 9. Glycerin | 55 | 16 | 10.8** | 0.20 | 0.24 | Very soft gel |
| 10. Glycerin | 30 | 16 | 10 | 0.10 | 0.06 | Very firm rubbery solid |
| 11. Glycerin | 10 | 36 | 10 | 0.10 | 0.06 | Hard rubbery solid |
| 12. Glycerin | 55 | 6 | 5.5 | 0.10 | 0.06 | Soft gel |
| 13. Glycerin | 55 | 6 | 20 | 0.10 | 0.06 | Firm rubbery solid |
| 14. DMF*** | 55 | 6 | 10 | 0.10 | 0.06 | Thick syrup |
| 15. DMF | 55 | 14 | 25 | 0.30 | 0.06 | Soft elastic gel |
| 16. DMF | 55 | 10 | 21 | 0.20 | 0.06 | Very soft elastic gel |

*DMSO - Dimethyl Sulfoxide
**The acrylic acid was neutralized to pH 7.0 before polymerization.
***DMF - Dimethyl formamide

EXAMPLE 2

The gel samples from formulations Nos. 1, 4, 6, 7, 8 and 15 of Table II were soaked in distilled water for various periods of time, followed by weighing to determine the amount of water absorption by gain in weight. The data from this series of experiments is set forth in Table III, where it will be seen that the gel formulations have excellent moisture absorption properties.

TABLE III

| [1]Sample | Soak Time, hr. | % Wt. Gain |
|---|---|---|
| Formulation 1 | 1 | 34.8 |
| " | 3 | 53.0 |
| " | 6 | 66.4 |
| " | 11 | 84.0 |
| " | 24 | 112.8 |
| Formulation 4 | 1.5 | 30.9 |
| " | 3 | 54.5 |
| " | 17 | 88.3 |
| " | 25 | 92.5 |
| " | 44 | 92.5 |
| Formulation 6 | 4 | 67.2 |
| " | 8 | 91.0 |
| " | 27 | 138.0 |
| " | 46.5 | 179 |
| Formulation 7 | 4 | 32.0 |
| " | 8 | 42.5 |
| " | 27 | 61.1 |
| " | 46.5 | 68.8 |
| Formulation 8 | 3.5 | 69.7 |
| " | 6.5 | 102.8 |
| " | 8 | 114.5 |
| " | 18 | 160 |
| " | 28 | 189 |
| " | 43 | 212 |
| Formulation 15 | 1.5 | 25.2 |
| " | 3.5 | 38.0 |
| " | 20 | 84.9 |

[1]From Table II

EXAMPLE 3

A gel body as set forth in Formulation 1 (Table II) was covered with a moisture and heatpermeable stretch cloth, whereupon the composite was placed in a chamber at 100% relative humidity and 40° C. This treatment was continued for a period of 45 hours, with moisture absorption being determined periodically by gain in weight of the gel body. After the moisture treatment, the product was placed in ambient air, and the moisture loss was determined by weight loss over time. Relative humidity during the ambient condition treatment was 50-95%, whereas the temperature ranged from 60-95° F. Duplicate runs using two gel bodies produced in accordance with Formulation 1 (Table II) were made. The data from this test is set forth in Table IV, where it will be seen that the gel bodies in accordance with the invention have the ability to both absorb moisture in high humidity conditions, and to desorb moisture when placed in lower moisture atmospheres.

TABLE IV

| Conditions | Time, hr. | Run 1 % Wt. gain | Run 2 % Wt. gain |
| --- | --- | --- | --- |
| Chamber | 1 | 11.2 | 5.9 |
| " | 4 | 14.1 | 14.7 |
| " | 18 | 20.9 | 20.6 |
| " | 23 | 23.9 | 23.7 |
| " | 45 | 28.6 | 29.4 |
| Ambient | 53 | 24.5 | 25.3 |
| " | 65 | 17.6 | 24.3 |
| " | 74.5 | 19.7 | 20.2 |
| " | 90 | 22.1 | 22.6 |
| " | 102 | 19.0 | 19.0 |

EXAMPLE 4

To 80 g of 50% acrylamide in water was added 0.06 g citric acid, 0.120 g Ammonium persulfate, and 0.235 g MBA. The resulting mixture was stirred for 10 minutes. Then 180 g of glycerin was added and the solution was mixed vigorously for 5 minutes, followed by the addition of 10.0 g of a drum dried hydrolyzed starch-acrylonitrile graft copolymer prepared as described in U.S. Pat. No. 3,935,099. The mixture was kept at room temperature for 18 hours and a yellow translucent gel was obtained.

A 27.0 g portion of the gel was submerged in 300 ml of distilled water and periodically removed and weighed to determine the water absorbance. These results are set forth below:

TABLE V

| Time | Wt (grams) | % gain |
| --- | --- | --- |
| 0 | 27.0 | 0 |
| 15 min. | 32.0 | 18.5 |
| 30 min. | 34.0 | 25.9 |
| 60 min. | 36.5 | 35.2 |
| 2 hrs. | 42.0 | 55.5 |
| 3 hrs. | 46.0 | 70.4 |
| 4 hrs. | 48.0 | 77.8 |
| 5 hrs. | 50.0 | 85.2 |
| 6 hrs. | 52.5 | 92.6 |
| 7 hrs. | 54.5 | 101.9 |
| 8 hrs. | 56.5 | 109.3 |
| 24 hrs. | 73.5 | 172.2 |

The gel bodies in accordance with the invention can be used in the context of therapy wraps in a wide variety of ways. To give but a few examples, the gel can be fabricated as an elongated strip which is encased within an appropriate stretch fabric. This composite can then be applied to various body parts such as elbows, knees and ankles, using for this purpose straps or other ties in order to hold the composite in place. Turning to the drawing, and particularly FIG. 1, it will be seen that such an elongated composite 10 is placed around the elbow of a patient and secured in place by means of a tie 12. In this instance the tie 12 is secured to one end of the elongated composite, and the tie is provided with appropriate Velcro strips for securing the entire composite 10 in place.

Figure 3:
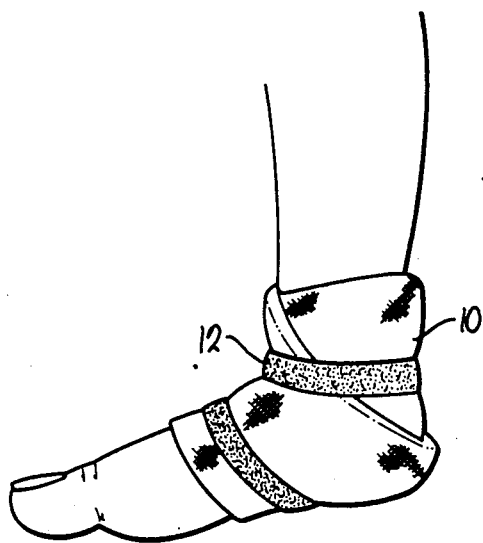
FIG. 3 is a view similar to that of FIG. 1, but depicts the elongated therapy wrap positioned about the ankle of an injured patient.

In like manner, FIG. 3 illustrates the composite 10 wrapped about the ankle of a patient, with the tie 12 being appropriately placed so as to secure the composite in position.

Figure 2:
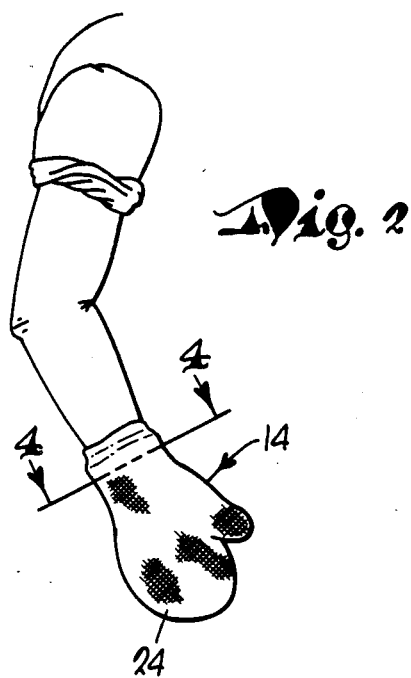
FIG. 2 is a view similar to that of FIG. 1, but a glove-shaped therapy member in accordance with the invention, placed over the hand and wrist of an injured patient.
Figure 4:
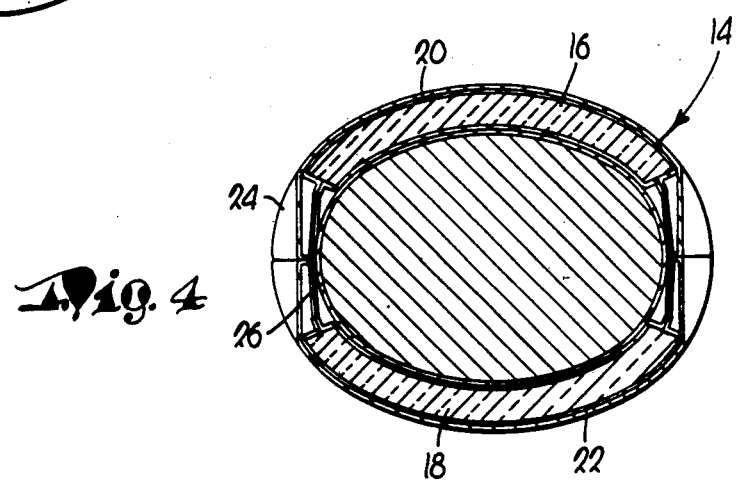
FIG. 4 is a sectional view taken along line 4—4 of FIG. 2 which depicts the internal construction of the glove-type therapy member.

FIGS. 2 and 4 on the other hand illustrate another exemplary embodiment of the invention. In this case, a glove or mitten composite 14 is provided which includes (see FIG. 4) a pair of mirror image, generally hand-shaped gel bodies which are separately encased within an inner fabric liner 20, 22 and sewn together. Outermost glove-shaped casing 24 is provided about the entirety of the sewn-together gel bodies, in order to complete the composite member.

In the use of such a glove-type composite, an inner fabric glove 26 is advantageously provided which is first slipped over the hand and wrist of the patient, followed by the composite 14.

In the case of heating of gel body composites in accordance with the invention, such can be accomplished by placing the composite in a conventional oven for ten minutes at 250° F., or by heating in a microwave oven for a period of from about one-half to three minutes, depending upon the type of composite being heated and the desired temperature of the gel.

It will of course be understood that the composites illustrated in the drawing are exemplary only, and that a variety of other shapes and sizes of therapy wraps can be employed. For example, wraps can be designed which are specifically configured for shoulder and upper arm application, or for application to the chest or legs of a patient.

I claim:

1. A method of treating a body part of a patient, comprising the steps of:
   providing a therapy member including a body of self-sustaining, non-flowable, pliable gel having a water soluble humectant entrapped within a polymeric matrix having therein acrylic acid or acrylamide monomer moieties, said gel body being at least partially encased within a moisture and heat-permeable cloth, said gel being characterized by the properties of maintaining said self-sustension and pliability over a temperature range of from about −20° to 350° F., and of absorbing and desorbing moisture through said cloth;
   pretreating said member by altering the temperature of said gel body to a level significantly below or above body temperature while maintaining the pliability and moisture sorbing characteristics of the body; and
   applying said pretreated member to said body part by placing said gel body in close, generally conforming proximity to the body part for heating or cooling of the body part.

2. The method as set forth in claim 1, including the step of completely encasing said gel body in said cloth.

3. The method as set forth in claim 1, including the step of affixing said pretreated member to said body part.

4. The method as set forth in claim 1, said humectant being present at a level of from about 20 to 85% by weight in said gel body.

5. The method as set forth in claim 1, said humectant being present from the group consisting of glycerin, ethylene glycol, propylene glycol, dimethyl sulfoxide and dimethyl formamide.

6. The method as set forth in claim 1, said matrix comprising a polymer of acrylamide.

7. The method as set forth in claim 1, said gel having a thickness of from about ¼ to 1½ inches.

8. The method as set forth in claim 1, including the step of altering the temperature of said gel body to a temperature within the range of from about −20° to 350° F.

9. The method as set forth in claim 1, said polymeric matrix being selected from the group consisting of the polymers, copolymers and terpolymers containing acrylic acid or acrylamide monomer moieties.

10. A method of treating injured skin, comprising the steps of:
providing a therapy member including a body of self-sustaining pliable gel, said gel comprising from about 10 to 25% by weight synthetic polymeric matrix, from about 10 to 50% by weight water, and a substantial quantity of water soluble humectant entrapped within said matrix, said gel body being characterized by the property of absorbing and desorbing moisture; and
placing said gel body in direct contact with said injured skin while said body retains said humectant entrapped therein, said matrix permitting, and said humectant being present at a level for, exchange of humectant when moisture is absorbed from said skin in order to keep skin moisture levels relatively low.

11. The method as set forth in claim 10, said matrix including acrylic acid or acrylamide moieties therein.

12. The method as set forth in claim 10, said humectant being present at a level of from about 20 to 85% by weight in said gel body.

13. The method as set forth in claim 10, said member consisting essentially of said gel body.

14. The method as set forth in claim 10, said humectant being selected from the group consisting of glycerin, ethylene glycol, propylene glycol, dimethyl sulfoxide and dimethyl formamide.

15. The method as set forth in claim 10, including the step of leaving said gel body in direct contact with said injured skin for a period of from about 2 to 21 days.

16. The method of claim 10, wherein the skin in direct contact with the gel body is burned.

17. The method as set forth in claim 11, said polymeric matrix being selected from the group consisting of the polymers, copolymers and terpolymers containing acrylic acid or acrylamide monomer moieties.

* * * * *